(12) United States Patent
Dalle et al.

(10) Patent No.: US 8,167,797 B2
(45) Date of Patent: May 1, 2012

(54) SHEATH FOR CONTAINING AND MANIPULATING OF A SINGLE-USE LARYNGOSCOPE BLADE AND USE OF A BLADE THUS CONDITIONED

(75) Inventors: Valery Dalle, Gouvieux (FR); Jean-Luc Carrez, Ecouen (FR); Andre Brouillon, Rosoy (FR)

(73) Assignee: Vygon, Ecouen (FR)

( * ) Notice: Subject to any disclaimer, the term of this patent is extended or adjusted under 35 U.S.C. 154(b) by 703 days.

(21) Appl. No.: 10/483,220

(22) PCT Filed: Mar. 14, 2003

(86) PCT No.: PCT/FR03/00822
§ 371 (c)(1),
(2), (4) Date: Jan. 8, 2004

(87) PCT Pub. No.: WO03/077736
PCT Pub. Date: Sep. 25, 2003

(65) Prior Publication Data
US 2004/0220454 A1    Nov. 4, 2004

(30) Foreign Application Priority Data
Mar. 15, 2002  (FR) .................................... 02/03227

(51) Int. Cl.
*A61B 1/267* (2006.01)

(52) U.S. Cl. ......... 600/186; 600/185; 600/190; 600/193
(58) Field of Classification Search .................. 600/185, 600/186, 198, 203, 121, 122, 124, 125, 193
See application file for complete search history.

(56) References Cited

U.S. PATENT DOCUMENTS

| | | | | |
|---|---|---|---|---|
| 4,522,196 A | * | 6/1985 | Cunningham et al. | 600/112 |
| 4,646,722 A | * | 3/1987 | Silverstein et al. | 600/104 |
| 4,741,326 A | * | 5/1988 | Sidall et al. | 600/123 |
| 4,878,485 A | * | 11/1989 | Adair | 600/122 |
| 4,878,486 A | * | 11/1989 | Slater | 600/186 |
| 4,972,825 A | * | 11/1990 | Vescovo, Jr. | 600/186 |
| 5,347,995 A | * | 9/1994 | Slater et al. | 600/190 |
| 5,695,454 A | * | 12/1997 | Mourkidou | 600/186 |
| 5,792,045 A | * | 8/1998 | Adair | 600/125 |
| 5,924,977 A | * | 7/1999 | Yabe et al. | 600/121 |

* cited by examiner

*Primary Examiner* — Matthew J Kasztejna
(74) *Attorney, Agent, or Firm* — Levine & Mandelbaum

(57) ABSTRACT

A sheath for containing and manipulating of a single-use laryngoscope blade is constituted by a closed outer bag (S) enabling its content to be sterilized and kept sterile, and an inner sheath (G) containing the blade between a closed end of the sheath and an open end of the sheath, the sheath being thin and tear-resistant so as to enable the blade to be mounted on the handle and separated therefrom without removing the sheath and so that the sheath can be turned inside out. The invention is applicable to packaging laryngoscope blades.

1 Claim, 3 Drawing Sheets

FIG_1
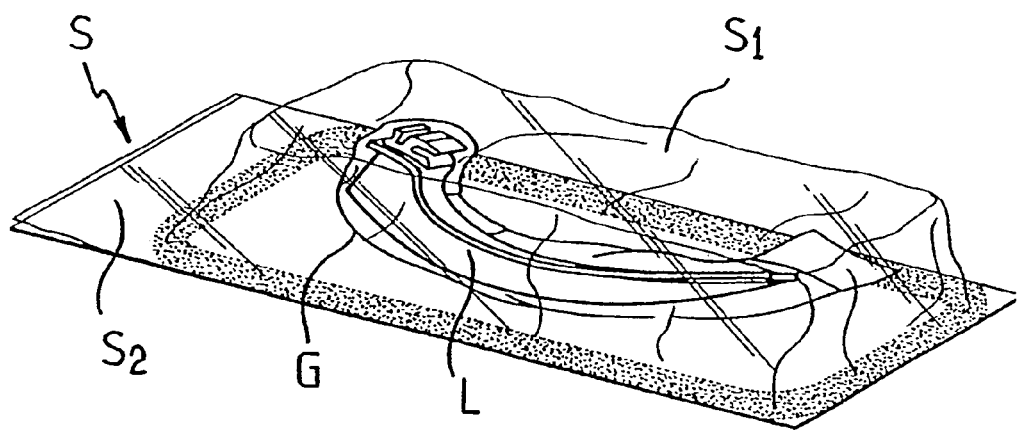
FIG_2
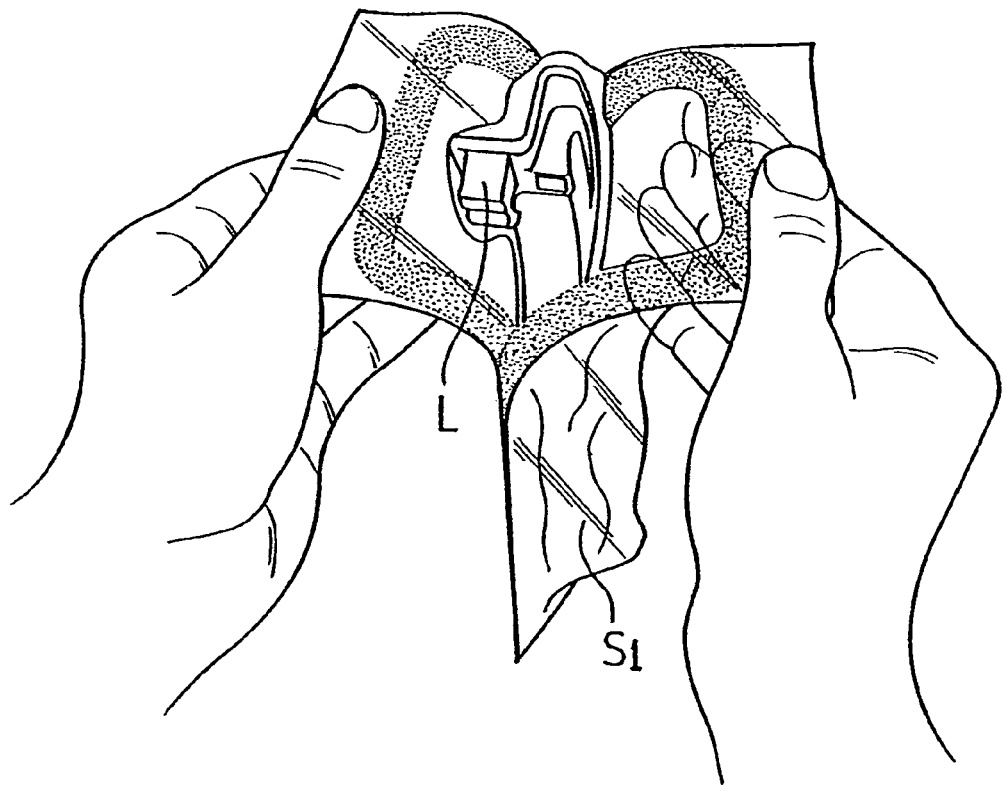

FIG_3
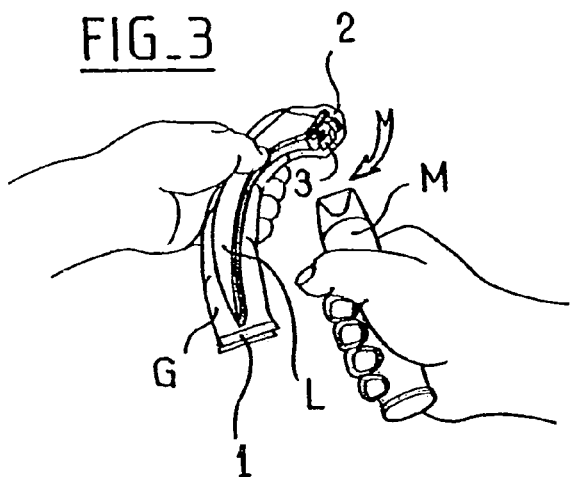
FIG_4
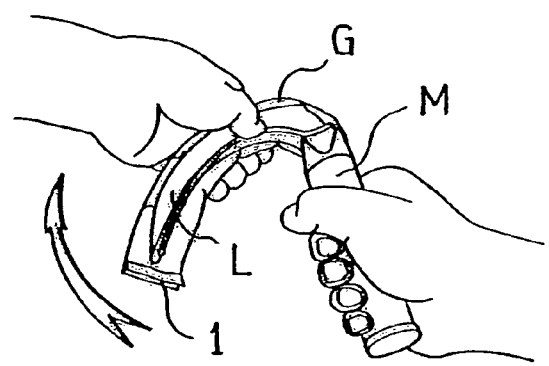
FIG_5
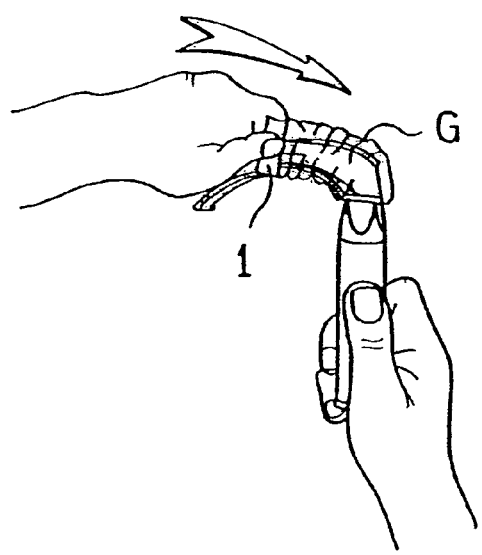
FIG_6
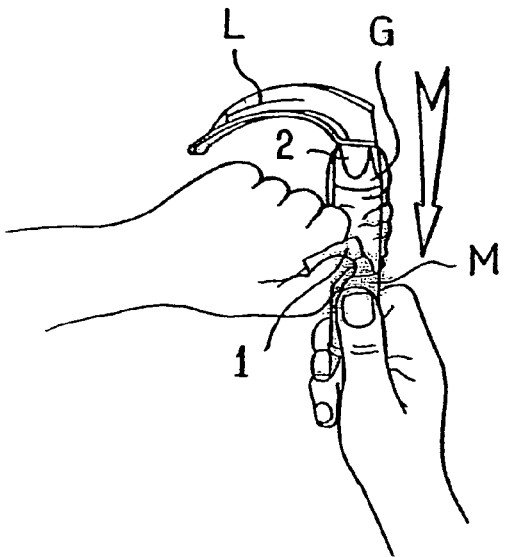

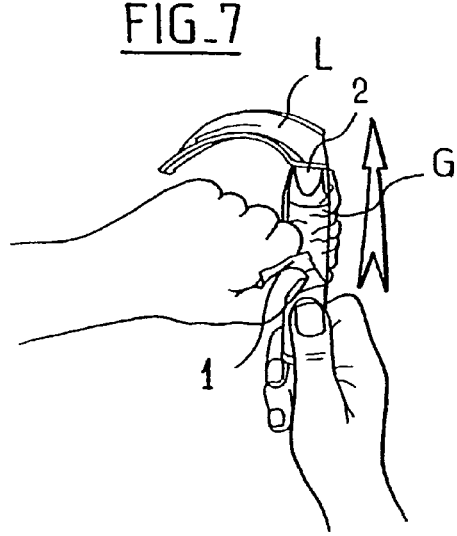
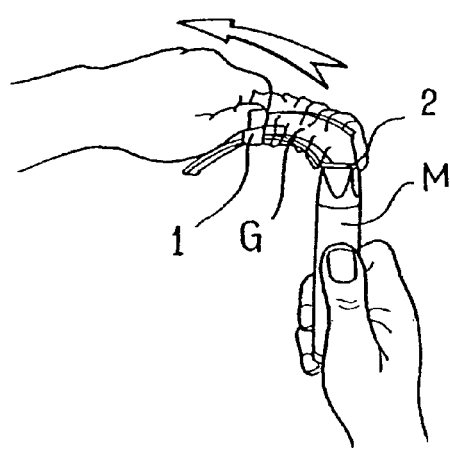
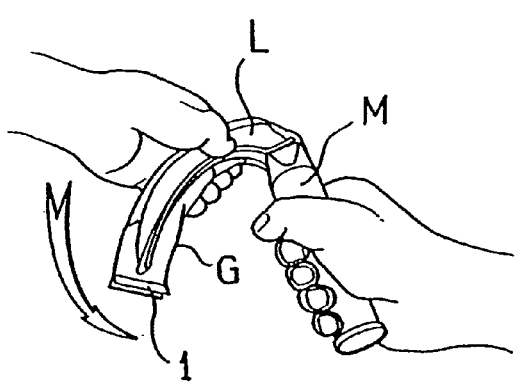
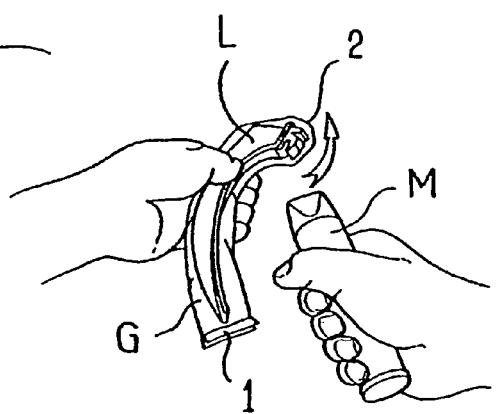

SHEATH FOR CONTAINING AND MANIPULATING OF A SINGLE-USE LARYNGOSCOPE BLADE AND USE OF A BLADE THUS CONDITIONED

BACKGROUND OF THE INVENTION

The invention relates to a sheath for containing and handling a single-use laryngoscope blade for being fastened detachably on a laryngoscope handle, and to the use of a blade packaged in this way.

Numerous examples are known of laryngoscope blades each presenting a fastening end adapted for mounting and hooking the blade on a matching receiver end of the handle: EP 0 110 333, EP 0 169 497, GB 1191949, etc.

Usually, the laryngoscope blade is packaged in sterile manner in packaging from which the blade is extracted in order to be fastened on a handle for use.

Publication U.S. Pat. No. 5,347,995 explains the difficulty of sterilizing a laryngoscope blade and recommends using sterile sheathing which presents an open end and a closed end and which is suitable for containing the blade and covering part of the laryngoscope handle. The user receives the sheath empty and packaged in protective packaging. In order to use a laryngoscope, the user fastens the blade on the handle, opens the package of the sheath, inserts the blade in the open end of the sterile sheath until the blade is contained inside the sheath which covers the end of the handle, and then fixes the sheath to said end; the user then removes the protective packaging and the laryngoscope is ready for use, the sheath remaining in place on the blade so as to ensure that the blade is sterile.

The sheath must be discarded after use (although the blade is designed to be reused), and it is designed to protect the patient from coming into contact with a non-sterile blade, however it does not protect the operator from a risk of becoming infected on contact with the patient.

SUMMARY OF THE INVENTION

An object of the present invention is to enable a practitioner to use a laryngoscope without risking infection and contamination.

An object of the present invention is to enable a practitioner to use a laryngoscope without risking infection and contamination.

According to the present invention, this is achieved by placing the blade in a sheath between an open or openable end of the sheath and an opposite end of the sheath that is closed, the blade being disposed in the sheath in such a manner that the fastening end of the blade is adjacent to the closed end of the sheath, said sheath being made of a film that is sufficiently thin, flexible, and tear-resistant so that the operator can take hold of the blade through the sheath in order to fasten the blade on the handle with the closed end of the sheath remaining interposed between the fastening end of the blade and the receiving end of the handle, and so that the sheath as held in this way can be turned inside out onto the handle so as to cover the handle and uncover the blade in order to allow the blade to be used, and can subsequently be turned back over the blade so as to cover the blade after it has been used and separated from the handle with the blade remaining inside the sheath which is discarded together with the blade.

The sheath is made, for example, out of fine film, typically film having a thickness of less an 100 micrometers (μm) and suitable for withstanding accidental tearing while the blade is being mounted or removed, in spite of the fineness of the film, and the film is sufficiently transparent so as to transmit light well.

Amongst the materials that are suitable for this purpose, polyurethane is presently a preferred material.

In one of its aspects, the invention also relates to use of a laryngoscope blade packaged in a sheath of the invention, which use comprises:

taking hold of the blade through the sheath to mount the blade on an appropriate handle;

the closed end of the sheath remaining interposed between the fastening end of the blade and the receiving end of the handle;

turning the sheath inside out onto the handle so as to uncover the blade in order to enable it to be used; and after the blade has been used by being inserted in the mouth of a patient, turning the sheath back over the blade, separating the blade from the handle, and discarding the sheath containing the blade.

DESCRIPTION OF THE DRAWINGS

There follows a description of an embodiment of the invention given reference to the figures of the accompanying drawings, in which:

FIG. 1 is a perspective view of an assembly comprising an outer bag of a closed package containing an inner sheath, itself containing a sterilized laryngoscope blade;

FIG. 2 is a perspective view of the FIG. 1 assembly after the outer bag has been opened; and FIGS. 3 to 10 show the various stages of implementing a blade packaged in a sheath of the invention.

DESCRIPTION OF THE PREFERRED EMBODIMENT

The outer bag (S) is a conventional bag, for example a bag that can be peeled open or a blister pack with a peel-off cover. By way of example, the bag is constituted by a flexible transparent film (S1) fixed on a support sheet (S2), the bag having porosity suitable for enabling gas or radiation to pass through the bag in order to sterilize the content thereof.

Once the bag has been opened, the inner sheath is extracted, which sheath contains a curved laryngoscope blade completely, e.g. a blade made of a non-metallic material such as a thermoplastic resin.

In FIG. 3 of the accompanying drawings, there can be seen the sheath (G), e.g. in the form of a thin transparent film of polyurethane containing the blade (L) and held in the hand of an operator.

In accordance with the invention, this sheath is a flexible tube with a very thin wall which presents an end (1) that is open or suitable for being opened and an opposite end (2) which is closed. In conventional manner, the blade presents an end (3) adapted to enable the blade to be mounted on one end of a handle (M) which the operator holds in the other hand. The blade is placed inside the sheath in such a manner that the mounting end (3) of the blade is adjacent to the closed end (2) of the sheath.

There is no need to describe this end of the blade in greater detail, nor the corresponding end of the handle (M), since they are well known in themselves in a variety of embodiments, and since the invention does not bear on them.

As can be see in FIG. 4, the operator fastens the blade on the end of the handle without the sheath impeding such fastening, because of the very small thickness of its wall.

Once fastening has been achieved, the operator turns the sheath inside out onto the handle as shown in FIGS. 5 and 6.

The laryngoscope is then ready for use in conventional manner.

After use, the sheath (G) is turned back onto the blade in the opposite direction (FIGS. 7 and 8) so that the blade and the sheath containing it again can be separated from the handle (FIGS. 9 and 10) and discarded. Advantageously, the open end of the sheath can present tabs to facilitate turning it back over the blade, thereby increasing protection for the operator against any risk of contact with the blade.

The invention is not limited to this embodiment.

The invention is not limited to a particular choice of means enabling the blade to be fastened on the handle, providing said means are suitable for not tearing the sheath. In the example shown in the figures, these means comprise, in conventional manner, a tab formed at the fastening end of the blade and a cavity suitable for receiving the tab formed at the receiving end of the handle, said tab presenting a hook-shaped tab portion and said cavity presenting a transverse bar on which the hook is engaged when mounting the blade on the handle; in addition the tab and the cavity include means for locking the blade when mounted on the handle. In the example shown, these locking means comprise a resilient wall on the tab of the blade and a second transverse bar in the cavity at the end of the handle, the resilient wall making resilient contact with said second bar when the blade is mounted on the handle.

The invention claimed is:

1. A method for the use of a sheath to contain and handle a laryngoscope blade having a fastening end adapted for detachably mounting the blade on a receiving end of a handle, the sheath having an open or openable end and an opposite end that is closed, said method comprising:

mounting the fastening end of the blade on the receiving end of the handle while holding the blade through the sheath, the closed end of the sheath remaining interposed between the blade and the handle;

turning the sheath inside out onto the handle so as to cover the handle and uncover the blade in order to enable it to be used;

after the blade has been used, turning the sheath back onto the blade;

separating the blade from the handle; and discarding the sheath containing the blade.

* * * * *